United States Patent
Mora Lopez et al.

(10) Patent No.: US 11,583,679 B2
(45) Date of Patent: Feb. 21, 2023

(54) ELECTRODE ARRANGEMENT FOR STIMULATING AND RECORDING ELECTRICAL SIGNALS IN BIOLOGICAL MATTER, A NEURAL PROBE, A MICRO-ELECTRODE ARRAY AND A METHOD FOR CONTROLLING AN ELECTRODE ARRANGEMENT

(71) Applicant: IMEC VZW, Leuven (BE)

(72) Inventors: Carolina Mora Lopez, Kessel-Lo (BE); Marco Ballini, Leuven (BE); Didac Gomez Salinas, Leuven (BE)

(73) Assignee: IMEC VZW, Leuven (BE)

( * ) Notice: Subject to any disclaimer, the term of this patent is extended or adjusted under 35 U.S.C. 154(b) by 195 days.

(21) Appl. No.: 17/031,733

(22) Filed: Sep. 24, 2020

(65) Prior Publication Data
US 2021/0085980 A1    Mar. 25, 2021

(30) Foreign Application Priority Data
Sep. 24, 2019 (EP) .................................... 19199302

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01); *A61N 1/3614* (2017.08); *A61N 1/3615* (2013.01); *A61N 1/36167* (2013.01)

(58) Field of Classification Search
CPC .............. A61N 1/36139; A61N 1/3614; A61N 1/0534; A61N 1/3615; A61N 1/36167
See application file for complete search history.

(56) References Cited

U.S. PATENT DOCUMENTS

2006/0224187 A1* 10/2006 Bradley ............. A61N 1/37241
607/2
2006/0247732 A1* 11/2006 Wesselink ............ A61N 1/0553
607/46

(Continued)

FOREIGN PATENT DOCUMENTS

| DE | 19928552 A1 | 1/2001 |
| WO | WO-2005/087309 A1 | 9/2005 |
| WO | WO-2010/025226 A1 | 3/2010 |

OTHER PUBLICATIONS

David A. Ksienski, "A Minimum Profile Uniform Current Density Electrode", IEEE Transactions on Biomedical Engineering, vol. 39, No. 7, pp. 682-692, Jul. 1992.

(Continued)

*Primary Examiner* — Ankit D Tejani
*Assistant Examiner* — Joshua Brendon Solomon
(74) *Attorney, Agent, or Firm* — Moser Taboada

(57) ABSTRACT

An electrode arrangement for stimulating and recording electrical signals in biological matter comprises:
  an array (110) of electrodes (112), wherein electrodes (112) are configured to be switchable between stimulating and recording of electrical signals;
  a control unit (120), wherein the control unit (120) is configured to select a plurality of electrodes (112) to form a combined macroelectrode site (114) for providing a stimulating signal,
  wherein the control unit (120) is further configured to determine a perimeter electrode (112b) and a central electrode (112a), wherein the perimeter electrode (112b) is arranged at a perimeter of the combined macroelectrode site (114) and the central electrode (112a) is arranged centrally within the combined macroelectrode site (114), and (Continued)

○ Recording Electrode
● Stimulation Electrode wherein the control unit (120) is further configured to provide a stimulation signal to the perimeter electrode (112*b*) that has a lower magnitude than a stimulation signal provided to the central electrode (112*a*).

15 Claims, 7 Drawing Sheets

(56) References Cited

U.S. PATENT DOCUMENTS

| | | | |
|---|---|---|---|
| 2006/0265039 A1 | 11/2006 | Bartic et al. | |
| 2007/0123765 A1 | 5/2007 | Hetke et al. | |
| 2010/0125315 A1* | 5/2010 | Parramon | A61N 1/36157 607/2 |
| 2011/0093052 A1 | 4/2011 | Anderson et al. | |
| 2012/0053659 A1* | 3/2012 | Molnar | A61N 1/3605 607/62 |
| 2013/0150931 A1 | 6/2013 | Kipke et al. | |
| 2015/0335257 A1 | 11/2015 | McNaughton et al. | |
| 2016/0101286 A1* | 4/2016 | Bhadra | A61N 1/3615 607/46 |
| 2017/0000368 A1 | 1/2017 | Raducanu et al. | |

OTHER PUBLICATIONS

Xuefeng Frank Wei, "Analysis and Design of Electrodes for Deep Brain Stimulation", Dissertation, Duke University, 2009.

Frey et al., "Switch-Matrix-Based High-Density Microelectrode Array in CMOS Technology", IEEE Journal of Solid-State Circuits, vol. 45, No. 2, pp. 467-482, Feb. 2010.

Song et al., "Optimal geometry toward uniform current density electrodes", Inverse Problems, vol. 27, No. 7, pp. 1-21, Jul. 2011.

Wang et al., "Reduction of Edge Effect on Disk Electrodes by Optimized Current Waveform", IEEE Transactions on Biomedical Engineering, vol. 61, No. 8, pp. 2254-2263, Aug. 2014.

Dmochowski et al., "Noninvasive Neuromodulation Goes Deep", Cell, vol. 169, p. 977, Jun. 1, 2017.

Tarnaud et al., "Investigation of the Stimulation Capabilities of a High-Resolution Neurorecording Probe for the Application of Closed-Loop Deep Brain Stimulation*", 2018 40th Annual International Conference of the IEEE Engineering in Medicine and Biology Society (EMBC), pp. 2166-2169, Jul. 18, 2018.

Nikolayev et al., "Proceedings #63: Low-Profile 3D Microelectronics with Near-Uniform Current Density for High-Resolution Neural Stimulation", Brain Stimulation, vol. 12, No. 4, pp. e155-e157, Aug. 1, 2019.

Extended European Search Report on Application No. EP19199302. 1, dated Mar. 19, 2020.

\* cited by examiner

○ Recording Electrode
◉ Stimulation Electrode

ELECTRODE ARRANGEMENT FOR STIMULATING AND RECORDING ELECTRICAL SIGNALS IN BIOLOGICAL MATTER, A NEURAL PROBE, A MICRO-ELECTRODE ARRAY AND A METHOD FOR CONTROLLING AN ELECTRODE ARRANGEMENT

CROSS-REFERENCE TO RELATED APPLICATIONS

This Application claims priority to European Patent Application No. 19199302.1, filed on 24 Sep. 2019, which is incorporated herein by reference in its entirety.

TECHNICAL FIELD

The present inventive concept relates to stimulating and recording of electrical signals in biological matter.

BACKGROUND

Electrical signals may be used for treating biological matter. Thus, a stimulating electrical signal may be provided in order to treat the biological matter. It may also be desired to record electrical signals propagating in the biological matter so as to enable analyzing an impact of the stimulating electrical signal. Electrical signals may also be used for analyzing activity and/or characteristics of biological matter, by providing a stimulating electrical signal and recording propagation of the electrical signal in the biological matter or recording electrical signals in the biological matter triggered by the stimulating electrical signal. Thus, it is of interest to stimulate and record electrical signals in biological matter, both for treating and analyzing biological matter.

Treatment of biological matter using electrical signals is for instance used in various applications relating to brain treatment and/or neuroscience research. In this respect, microelectrodes may be implanted in the brain to deliver stimulation pulses to brain tissue, and an electrical pulse generator may generate stimulation pulses and is connected to the electrodes. For instance, this may be used in neural probes, neural prostheses, fundamental neuroscience research and/or in deep brain stimulation (DBS).

Effective stimulation of tissue requires that the charge/current injected must exceed certain threshold. However, as the charge increases, an overpotential of the electrode increases which may cause damage to the tissue or the electrode.

Efficacy of DBS therapy can be improved by localizing the current delivery into specific populations of neurons and by increasing the power efficiency through a suitable choice of electrode geometrical characteristics. Thus, significant research efforts have been done to find the best electrodes material, shapes and geometrical distributions to achieve both: 1) uniform current density (so as to have control over a safe injected charge to avoid tissue damage and/or electrode corrosion) and 2) power efficiency in localized stimulation.

A size of the electrodes may determine a resolution of treatment and/or analysis. Thus, a small size of the electrodes may be preferred. Also, a probe to be inserted into the brain may preferably be as small as possible to minimize tissue damage during implantation, which may also drive electrodes to have a small size. However, it is realized that as a surface area of a stimulation electrode decreases, the charge density will be increased. Therefore, there is a risk of tissue damage and/or electrode corrosion. In an electrode arrangement, stimulation electrodes may be larger than recording electrodes so as to avoid tissue damage and/or electrode corrosion associated with charge density of the stimulation electrode.

In US 2007/0123765, a customizable multichannel microelectrode array is disclosed. Some embodiments comprise two or more electrode sites grouped to form a larger composite site that enables tuning the neural interface region for recording and/or stimulation.

In US 2011/0093052, a neural interface system including an electrode array is disclosed. A plurality of electrode sites can be activated individually or in selectable groups of electrode sites. Additionally, each of the electrode sites may be activated with an independent activation intensity.

The use of electrode arrays for selecting a group of electrode sites for recording and/or stimulation may enable control of a resolution of treatment and/or analysis, but there may still be room for improvement in an efficacy of the treatment and/or analysis.

SUMMARY

It is an object of the present inventive concept to provide an electrode arrangement that enables stimulating and recording electrical signals in biological matter using a high resolution while having effective stimulation. In particular, it is an object of the present inventive concept to enable recording of electrical signals with a high resolution in the same local area in which stimulation is provided.

These and other objects of the invention are at least partly met by the invention as defined in the independent claims. Preferred embodiments are set out in the dependent claims.

According to a first aspect of the present inventive concept, there is provided an electrode arrangement for stimulating and recording electrical signals in biological matter, said electrode arrangement comprising: an array of electrodes, wherein electrodes in the array are configured to be switchable between stimulating and recording of electrical signals; a control unit for controlling functionality of electrodes in the array of electrodes, wherein the control unit is configured to select a plurality of electrodes of the array to be included in a group forming a combined macroelectrode site for providing a stimulating signal, wherein the control unit is further configured to determine at least one perimeter electrode within the selected plurality of electrodes and at least one central electrode within the selected plurality of electrodes, wherein the perimeter electrode is arranged at a perimeter of the combined macroelectrode site and the central electrode is arranged centrally within the combined macroelectrode site, and wherein the control unit is further configured to provide individually controlled stimulation signals to the selected plurality of electrodes, wherein the stimulation signal provided to the at least one perimeter electrode has a lower magnitude than the stimulation signal provided to the at least one central electrode.

Thanks to the electrodes in the array being switchable between a functionality of providing a stimulating electrical signal and a functionality of recording an electrical signal, a location of stimulation electrodes and recording electrodes may be dynamically defined during use of the electrode arrangement. This implies that a location of providing a stimulating electrical signal is not fixed in the electrode arrangement so as to allow shifting the location of providing the stimulating electrical signal. For instance, a neural probe comprising the electrode arrangement need not be moved within brain tissue (which may otherwise cause damage to the brain tissue) in order to move the location of providing the stimulating electrical signal.

Typically, a stimulation electrode may require a low impedance in order to limit an overpotential of the stimulation electrode and, therefore, the stimulation electrode may need to be large. Thanks to the possibility to select electrodes to be included in a group forming a combined macroelectrode, individual electrodes may be small while enabling a large combined macroelectrode to be formed. Thus, the small individual electrodes enable recording of signals with high resolution, while the possibility of grouping electrodes to form a combined macroelectrode enables a stimulation electrode of a sufficiently large size to be formed so as to avoid large overpotentials of the stimulation electrode.

Also, the possibility of grouping electrodes to form a combined macroelectrode enables an accurate control of a position of the macroelectrode in the electrode arrangement. By changing some of the electrodes that are included in the macroelectrode, a center of the macroelectrode may be moved in small steps, e.g. corresponding to a pitch of electrodes in the array, so that a localization of stimulation may be controlled with a high resolution.

Further, the control unit is configured to determine perimeter electrode(s) and central electrode(s) within the combined macroelectrode site. This implies that the electrodes within the selected plurality of electrodes forming the combined macroelectrode may be provided with different stimulation signals depending on whether the electrode is a perimeter electrode or a central electrode. The use of the individually controlled stimulation signals enables the control unit to control a current density over an area of the macroelectrode.

Thanks to the stimulation signal provided to the perimeter electrode(s) having a lower magnitude than the stimulation signal provided to the central electrode(s), charge accumulation or high current density at a perimeter of the combined macroelectrode site may be avoided or reduced. This implies that tissue damage and/or electrode corrosion at the perimeter may be avoided, while the stimulation signal may be sufficiently large e.g. so as to provide effective stimulation, which may be used e.g. in neural probes, neural prostheses, fundamental neuroscience research, and DBS therapy.

As used herein, the term "biological matter" should be construed as including any type of matter of a living organism or originating from a once-living organism. Thus, the biological matter may be tissue of a human being or another living organism, so that the electrode arrangement may be used arrangement for stimulating and recording electrical signals in vivo. However, the biological matter may alternatively be laboratory grown cells or a cell sample from a living organism, so that the electrode arrangement may be used arrangement for stimulating and recording electrical signals in vitro.

It should be realized that a number of electrodes included in a group forming a combined macroelectrode site could vary substantially. For instance, a group may be formed by three electrodes arranged on a line, wherein the two electrodes at ends of the line would be determined as perimeter electrodes and the electrode between the perimeter electrodes would be determined as a central electrode. However, it should be realized that the group may typically be formed by a larger number of electrodes, such as five electrodes with one central electrode being surrounded by perimeter electrodes in each direction horizontally and vertically from the central electrode. According to other alternatives, the number of electrodes may be in a range of 5-50, but larger numbers of electrodes may also be used.

A perimeter of the combined macroelectrode site may be defined as a line enclosing the plurality of electrodes selected to be included in the group. The perimeter electrodes may be arranged close to the line enclosing the electrodes, whereas the central electrodes may be arranged far away from the line.

It should also be realized that the control unit providing individually controlled stimulation signals need not necessarily provide unique stimulation signals to each electrode in the plurality of electrodes. Rather, if several perimeter electrodes are determined, each perimeter electrode may receive an equal signal. Similarly, if several central electrodes are determined, each central electrode may receive an equal signal. Also, the control unit may determine several sub-groups of electrodes within the selected plurality of electrodes, wherein each electrode in a sub-group may receive an equal signal. For instance, the electrodes in a sub-group may form rings of electrodes equidistantly arranged from a center of the group that may form a substantially circular overall shape.

By providing individually controlled stimulation signals, the control unit ensures that there is at least a difference in the stimulation signal provided to the at least one perimeter electrode and the at least one central electrode. Also, since it may not be known in advance which electrodes may be used as central electrodes and which electrodes may be used as perimeter electrodes, each electrode in the array of electrodes may, according to some embodiments, have a unique conductor line for receiving an individually controlled stimulation signal, such that the electrode is not pre-grouped with any other electrode in the array.

It should also be realized that even though the electrode arrangement provides a possibility of selecting electrodes to be included in a group for providing a stimulation signal from a combined macroelectrode site, the electrode arrangement may also be used for providing stimulation signals from single electrodes, so that a group need not always be defined when a stimulation signal is to be provided.

It should also be realized that the control unit may be configured to select electrodes to be included in separate groups so that more than one combined macroelectrode site may be simultaneously defined in the array of electrodes.

As used herein, the term "array of electrodes" should be construed as electrodes arranged in a regular manner. The electrodes may be arranged in rows and columns. However, the electrodes need not necessarily be arranged to form rows and columns. For instance, rows of electrodes may be provided, wherein every other row is shifted so that the electrodes are arranged to be diagonally placed between two adjoining electrodes of the adjacent rows.

As used herein, the term "lower magnitude" would, if the stimulation signal is a sine wave, imply that the stimulation signal having a lower magnitude has a lower peak or lower amplitude. The term "lower magnitude" may also be construed as a lower total power provided in the stimulation signal, e.g. if different waveforms would be provided to the at least one perimeter electrode and the at least one central electrode. In such case, a peak value of the stimulation signal may be equal.

It should also be realized that the stimulation signals provided to the selected electrodes included in the group need not differ only in magnitude. Thus, the stimulation signals may also differ in one or more of waveform, phase, and frequency.

According to an embodiment, each electrode in the array has a planar surface for contacting biological matter.

This implies that manufacturing of the array of electrodes is facilitated, since the electrodes need not be manufactured with complicated geometrical shapes. Further, thanks to the controlling of stimulation signals to be provided to electrodes selected to be included in the group forming a combined macroelectrode site, charge accumulation at a perimeter of the combined macroelectrode site may still be avoided or reduced.

However, it should be realized that even though the individually controlled stimulation signals may allow electrodes having a planar surface to be used, the electrode arrangement may alternatively comprise electrodes having shapes and geometrical distributions intended at improving uniformity of current density over the electrode surface. In such case, the controlling of the stimulation signals to the electrodes selected to be included in the group may further reduce charge accumulation at the perimeter of the combined macroelectrode site.

According to an embodiment, the array of electrodes is formed by a semiconductor manufacturing process. Semiconductor manufacturing is suitable for forming small structures that include electrical circuitry and may hence be suitable for manufacturing of at least the array of electrodes of the electrode arrangement. For instance, the electrode arrangement may be formed on a silicon substrate.

According to an embodiment, the array of electrodes is formed by thin-film technology. Thin-film technology may use semiconductor materials, but it should be realized that other materials may also or alternatively be used.

Thin-film technology may be particularly useful for manufacturing of planar objects, such as electrodes having a planar surface. Thin-film technology may allow forming of the array of electrodes on a flexible substrate. This may be particularly useful for providing an electrode arrangement that may be used in a neural probe with a very small impact on brain tissue during implantation. The thin-film technology may be used for depositing one or more layers of thin films for forming the array of electrodes, conductor lines and any circuitry associated with the array of electrodes. The thin-film technology may be used to form planar shapes with no need for special manufacturing processes, as the electrodes are provided with a planar surface.

According to an embodiment, each of the electrodes in the array has an equal size and shape.

The electrodes may have any shape, such as circular, square, hexagonal, octagonal, etc. However, a circular shape may be preferred as circular electrodes may be associated with a smaller charge accumulation at the perimeter compared to other shapes.

Having electrodes of equal size and shape may simplify manufacturing of the electrode arrangement, as identical elements are to be formed. Also, electrodes with equal size and shape may provide a high flexibility in forming of combined macroelectrode sites, as there is no difference in possible shapes of the macroelectrode site that may be formed depending on what electrodes of the array that are to be included.

According to an embodiment, an electrode may be circular with a diameter of a 10-20 μm. However, it should be realized that many other sizes are possible or suitable, e.g. depending on an application in which the electrode arrangement is to be used. For instance, the electrode may have a diameter of a few μm. A size of the combined macroelectrode site to be used may vary substantially on an application in which the electrode arrangement is to be used. However, the combined macroelectrode site may typically be larger than 40 μm and may in some embodiments be larger than 200 μm. This implies that the group forming a combined macroelectrode site may e.g. comprise 5-400 electrodes depending on the application.

According to an embodiment, each electrode of the array is connected to an individual conductor line for receiving stimulating signals or providing recorded signals.

In other words, a plurality of conductor lines is provided, and that each single electrode is associated with a single conductor line in a unique one-to-one relationship between electrodes and conductor lines.

Since each electrode is connected to an individual conductor line, it is possible to provide a unique stimulation signal to each of the electrodes. Thus, arbitrary shapes of the combined macroelectrode site may be formed within the array of electrodes and a high flexibility in the forming of the combined macroelectrode site is provided.

According to an embodiment, the selected plurality of electrodes is configured to be connected to a common current source or a common voltage source, wherein a resistance of each of the individual conductor lines is tunable for controlling a magnitude of the stimulation signal received by each electrode in the selected plurality of electrodes.

This is a simple solution, which may be implemented with simple circuitry (e.g. using just a transistor with tunable gate voltage). However, a resistance value needs to be comparable to electrode impedance to achieve current tunability, which also means that a significant voltage will drop on the tunable resistance. Also, a signal going to each of the selected plurality of electrodes is not fully independent of the signal going to other electrodes.

According to another embodiment, each of the individual conductor lines is connected to an individual programmable current source or an individual programmable voltage source for controlling a magnitude of the stimulation signal received by each electrode in the selected plurality of electrodes.

This implies that the stimulation signal received by each electrode may be flexibly controlled in complete independence of signals to other electrodes. However, it requires a more complex circuitry and may hence require a larger area for implementation.

According to an embodiment, the control unit stores pre-determined configurations for stimulation patterns for providing stimulation signals to the selected plurality of electrodes in different settings of the group forming a combined macroelectrode site.

This implies that suitable stimulation patterns can be determined in advance, e.g. analytically, such as through simulation software, or through tests, such as saline tests or in vitro tests on biological preparations (for example, cell cultures or tissue samples). Thus, the control unit may store the pre-determined configurations so as not to need to perform advanced computation for determining suitable stimulation signals when the electrode arrangement is to be used. This implies that the determining of the stimulation signals may be very fast and less processing resources may be required by the control unit (which may be particularly useful e.g. if the control unit is arranged in a portable device).

The pre-determined configurations may be common for any electrode arrangement or may be calibrated for individual specimen of the electrode arrangement after manufacturing of the electrode arrangement.

Also, a pre-determined configuration may be used as an initial setting for stimulation patterns that may be adapted based on feedback when the pre-determined configuration is used.

According to an embodiment, the control unit is configured to receive at least one feedback electrical signal recorded from the biological matter in response to a stimulating signal, wherein the control unit is further configured to adapt the individually controlled stimulation signals to the selected plurality of electrodes in dependence of the received at least one feedback electrical signal and/or adapt a selection of the plurality of electrodes of the array to be included in the group forming a combined macroelectrode site.

The feedback electrical signal may provide input of an efficacy of the stimulation signal, which may be used for improving stimulation efficacy. The feedback electrical signal may be recorded by an electrode in the array of electrodes for providing the feedback electrical signal to the control unit.

The adapting of the individually controlled stimulation signals may change one or more of a magnitude, waveform, phase or frequency of one or more of the stimulation signals. Also or alternatively, a selection of the electrodes to be included in the group forming the combined macroelectrode site may be changed.

According to an embodiment, the electrode arrangement further comprises monitoring circuitry, wherein the monitoring circuitry is associated with each electrode for monitoring an electrode voltage and/or impedance of the electrode, wherein the control unit is further configured to receive feedback from the monitoring circuitry in relation to the selected plurality of electrodes and to adapt the individually controlled stimulation signals to the selected plurality of electrodes in dependence of the received feedback from the monitoring circuitry.

Thanks to the monitoring circuitry, it may be possible to monitor the electrode voltage so as to ensure that electrode damage is avoided. For example, the feedback from the monitoring circuitry may be used to ensure that the electrode voltage does not exceed a water window, i.e. to ensure that the electrode voltage does not cause water to get electrolyzed.

According to an embodiment, the control unit is further configured to provide different stimulation signals to different electrodes within the selected plurality of electrodes with respect to at least one of waveform, phase and delay of the stimulation signal.

This may be used for steering of a stimulation in the biological matter. For instance, a location in the biological matter that receives the stimulation signal from the combined macroelectrode site may be changed based on changing the waveform, phase or delay of the stimulation signal.

Change of delay of the stimulation signal may be used with a pulse-based waveform, wherein a start time of the waveform is dependent on the time delay.

According to a second aspect of the present inventive concept, there is provided a neural probe comprising a carrier and the electrode arrangement according to the first aspect, wherein the carrier is adapted for being inserted into neural tissue of a brain and wherein at least the array of electrodes of the electrode arrangement is arranged on the carrier.

Effects and features of this second aspect are largely analogous to those described above in connection with the first aspect. Embodiments mentioned in relation to the first aspect are largely compatible with the second aspect.

Neural probes may preferably be as small as possible in order to limit impact on brain tissue during implantation. Thus, having small electrodes in an electrode arrangement is particularly useful when the electrode arrangement is used in a neural probe.

Thanks to the electrode arrangement of the present inventive concept, small electrodes may be combined into a macroelectrode site so as to provide a stimulation electrode with a limited overpotential.

Also, in different applications and types of neural stimulation (microstimulation and macrostimulation), different electrode sizes and current levels may be required. The possibility of selecting electrodes to be included in a group forming the macroelectrode site enables the neural probe to be used in different applications.

According to an embodiment, the neural probe also comprises at least one electrical stimuli generator connected to the electrodes. The electrical stimuli generator may receive input from the control unit and may then transmit the individual stimulation signals to the selected electrodes. The stimulation signals may be one or more electrical pulses, but other waveforms may also be used.

According to a third aspect of the present inventive concept, there is provided a micro-electrode array, comprising a carrier providing a surface for receiving a sample of biological matter; and the electrode arrangement according to the first aspect, wherein at least the array of electrodes is arranged on the carrier for recording electrical signals in the sample of biological matter.

Effects and features of this third aspect are largely analogous to those described above in connection with the first and second aspects. Embodiments mentioned in relation to the first and second aspects are largely compatible with the third aspect.

It may typically be desired to use a micro-electrode array in vastly different manners depending on the application or sample that is to be analyzed using the micro-electrode array. Therefore, the possibility in the electrode arrangement to dynamically define groups forming combined macroelectrode sites may be particularly useful in a micro-electrode array.

Furthermore, thanks to the control unit of the electrode arrangement controlling stimulation signals to perimeter electrode(s) and central electrode(s) in macroelectrode sites, electrode corrosion in the micro-electrode array may be avoided.

According to a fourth aspect of the present inventive concept, there is provided a method of controlling an electrode arrangement for stimulating and recording electrical signals in biological matter, wherein the electrode arrangement comprises an array of electrodes, wherein electrodes in the array are configured to be switchable between stimulating and recording of electrical signals, said method comprising: selecting a plurality of electrodes of the array to be included in a group forming a combined macroelectrode site for providing a stimulation signal; determining at least one perimeter electrode within the selected plurality of electrodes and at least one central electrode within the selected plurality of electrodes, wherein the perimeter electrode is arranged at a perimeter of the combined macroelectrode site and the central electrode is arranged centrally within the combined macroelectrode site, controlling stimulation signals to be provided to the selected plurality of electrodes, wherein the stimulation signal provided to the at least one perimeter electrode has a lower magnitude than the stimulation signal provided to the at least one central electrode.

Effects and features of this fourth aspect are largely analogous to those described above in connection with the first, second, and third aspects. Embodiments mentioned in relation to the first, second, and third aspects are largely compatible with the fourth aspect.

The method allows dynamically defining stimulation signals for different settings of combined macroelectrode sites so as to limit charge accumulation or high current density or voltage at the perimeter of the combined macroelectrode site and avoid causing tissue damage and/or electrode corrosion.

It should be realized that the controlling of the stimulation signals implies that the stimulation signals to be provided to the selected electrodes is determined, but the actual providing of the signal to the electrode is not part of controlling of the stimulation signal. Rather, the controlling may provide a control signal to a stimuli generator, which in turn, based on the control signal, transmits the stimulation signal to the electrode.

According to an embodiment, the method further comprises receiving at least one feedback electrical signal recorded from the biological matter in response to a stimulating signal and/or receiving feedback from a monitoring circuitry, which is associated with each electrode for monitoring an electrode voltage and/or impedance of the electrode, in relation to the selected plurality of electrodes, and adapting stimulation based on the received feedback.

The feedback may thus allow adaptation of stimulation signals to be provided to electrodes so as to improve efficacy of stimulation signals from the combined macroelectrode site and/or to avoid tissue damage and/or electrode corrosion at an electrode surface.

According to an embodiment, said adapting of stimulation comprises at least one of: changing a selection of electrodes to be included in the group forming the combined macroelectrode site, and changing one or more stimulation signals to the selected plurality of electrodes with respect to at least one of magnitude, waveform, phase and delay of the stimulation signal.

These are different ways of changing the stimulation provided by the combined macroelectrode site and adapting of stimulation may use one or more of the ways of changing the stimulation based on received feedback.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1A:
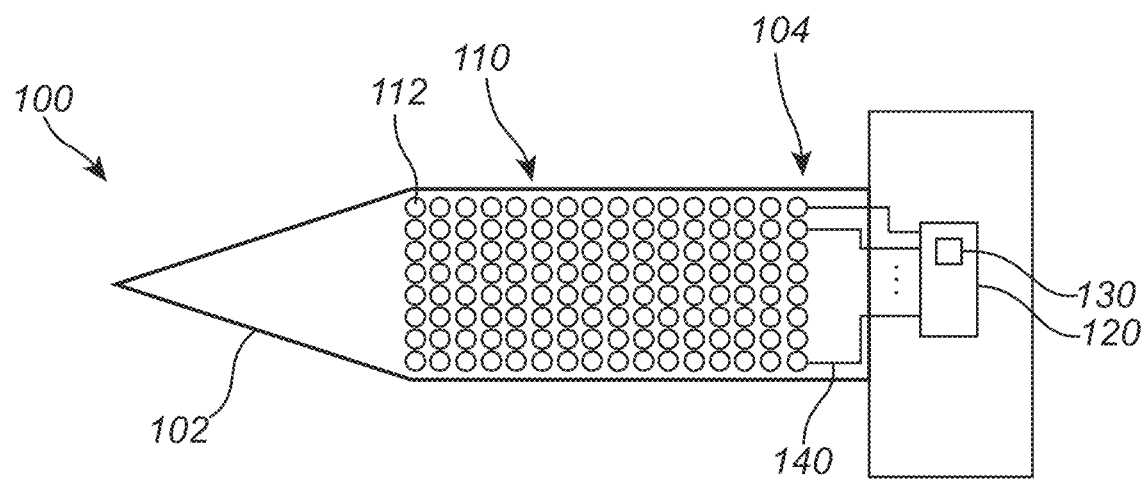
FIGS. 1a-b are schematic illustrations of a neural probe including an electrode arrangement according to an embodiment.
Figure 1B:
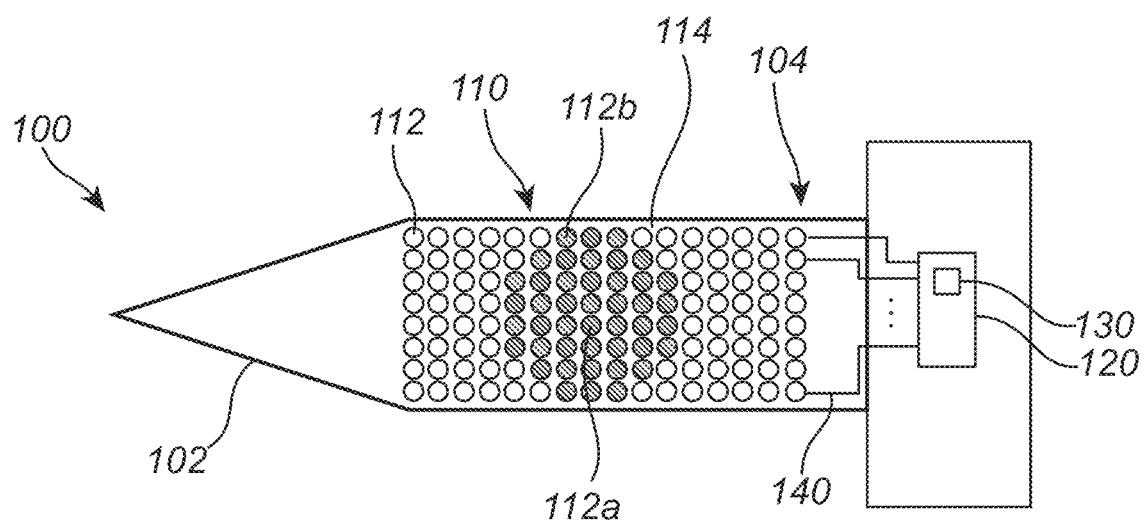

FIGS. 1a-b illustrate a neural probe 100. The neural probe 100 comprises a carrier 102, in this case in the form of a needle, which is configured to be inserted into neural tissue of a brain.

The carrier 102 is configured to carry an electrode arrangement 104 comprising an array 110 of electrodes 112. Each electrode 112 or at least a subset of the electrodes 112 in the array 110 may be switchable between stimulating and recording of electrical signals.

The electrodes 112 may have a small size and may thus enable a high resolution of recording of electrical signals, as illustrated in FIG. 1a, wherein each electrode 112 is set to record electrical signals for recording electrical signals with a high resolution.

The electrodes 112 may have any shape, such as circular, square, hexagonal, octagonal, etc. However, a circular shape may be preferred as circular electrodes 112 may be associated with a smaller charge accumulation at the perimeter compared to other shapes.

Having electrodes 112 of equal size and shape may enable a flexibility in grouping of electrodes to macroelectrode sites (as explained below). Having equal sizes and shapes of the electrodes 112 imply that it is possible to form macroelectrode sites in the same manner throughout the electrode arrangement 104.

The electrodes 112 may have a planar surface, which may facilitate forming of the electrodes 112 using a semiconductor manufacturing process or thin-film technology. Thus, manufacturing of the electrode arrangement 104 may be simple and not require forming of complex geometrical structures. Also, connections to the electrodes 112, such as conductor lines, as well as circuitry associated with the electrodes 112 may be manufactured using the semiconductor manufacturing process or thin-film technology.

However, it should be realized that, even when manufacturing electrodes 112 using thin-film technology, the electrodes 112 may be shaped, such as providing recessed electrodes for reducing charge accumulation at a perimeter of the electrode 112, when the electrode 112 is used for providing a stimulating signal.

As illustrated in FIG. 2b, the small electrodes 112 may be grouped (indicated by filled circles) to form a combined macroelectrode site 114. The combined macroelectrode site 114 may thus define a larger area than the individual electrodes 112 within the combined macroelectrode site 114.

A current density at a surface of the electrode 112 acting as a stimulation electrode may not be uniform, especially if the electrode 112 has a planar surface. In particular, due to non-uniform current density, charge accumulation may occur at a perimeter of the electrode 112. Also, when a combined macroelectrode site 114 is defined by grouping a plurality of electrodes 112, charge accumulation may occur at a perimeter of the combined macroelectrode site 114.

However, as realized in the present inventive concept, charge accumulation may be reduced by applying different currents to different electrodes 112 in the group forming the combined macroelectrode site 114. Larger currents may be provided to electrodes 112a far away from the perimeter and smaller currents may be provided to electrodes 112b close to the perimeter. In this way, it is possible to better distribute the current density over the entire surface of the combined macroelectrode site 114, reducing a risk of electrode corrosion and tissue damage at the perimeter of the combined macroelectrode site 114 and hence achieving more efficient localized stimulation.

Arbitrary shapes of the combined macroelectrode site 114 may be defined based on selecting the plurality of electrodes 112 to be included in the group forming the combined macroelectrode site 114.

In different applications and types of neural stimulation (microstimulation and macrostimulation), different electrode sizes and current levels may be required. The possibility of selecting electrodes 112 to be included in a group forming the macroelectrode site 114 enables the neural probe 100 to be used in different applications. Also, the possibility of selecting electrodes 112 to be included in a group forming the macroelectrode site 114 enables controlling of a location in which stimulation is to be provided, after the neural probe 100 has been implanted into brain tissue.

Also, the possibility of grouping electrodes 112 to form a combined macroelectrode site 114 enables an accurate control of a position of the macroelectrode site 114 in the electrode arrangement 104. By changing some of the electrodes 112 that are included in the macroelectrode site 114, a center of the macroelectrode site 114 may be moved in small steps, e.g. corresponding to the pitch of electrodes 112 within the array 110 (i.e. a size of the individual electrode 112+a spacing between electrodes 112), so that a localization of stimulation may be controlled with a high resolution.

The electrode arrangement 104 may further comprise a control unit 120. The control unit 120 may control functionality of the electrodes 112 in the array 110, by selecting which electrodes 112 are to receive stimulation signals and selecting which electrodes 112 that are to be used for reading a recorded signal.

The control unit 120 may thus selectively provide a stimulation signal to an electrode 112, so that the electrode 112 will function as a stimulation electrode or acquire a signal from an electrode 112 for using the electrode 112 to record electrical signals in tissue.

The control unit 120 is configured to control forming of combined macroelectrode sites 114. The control unit 120 may thus select which electrodes 112 are to be included in a group forming a combined macroelectrode site 114. The control unit 120 may further determine a location of electrodes within the combined macroelectrode site 114 so as to enable defining at least one electrode 112 as a perimeter electrode 112b and defining at least one electrode 112 as a central electrode 112a.

The control unit 120 is further configured to control stimulation signals to be provided to the selected plurality of electrodes 112, so that different signals are provided to different electrodes 112. In particular, the stimulation signal provided to a perimeter electrode 112a may have a lower magnitude than the stimulation signal provided to a central electrode 112b.

If several perimeter electrodes 112b are determined, each perimeter electrode 112b may receive an equal signal. Similarly, if several central electrodes 112a are determined, each central electrode 112a may receive an equal signal. Also, the control unit 120 may determine several sub-groups of electrodes 112 within the selected plurality of electrodes 112, wherein each electrode 112 in a sub-group may receive an equal signal. For instance, the electrodes 112 in a sub-group may form rings of electrodes 112 equidistantly arranged from a center of the group that may form a substantially circular overall shape.

However, it should also be realized that the control unit 120 may be configured to determine unique stimulation signals for each of the electrodes 112 in the group.

The control unit 120 may store pre-determined configurations for stimulation patterns such that stimulation signals to be provided to a selected plurality of electrodes 112 may be available in the stored pre-determined configuration. The pre-determined configurations may be available for a plurality of settings of the group, such as different sizes and shapes of the combined macroelectrode site 114.

The pre-determined configurations may be determined in advance, e.g. analytically, such as through simulation software, or through tests, such as saline tests or in vitro tests on biological preparations.

However, as an alternative, the control unit 120 may be configured to calculate or determine suitable stimulation signals to be provided to electrodes 112 in the group forming the combined macroelectrode site 114, when the macroelectrode site 114 is defined.

The control unit 120 may be implemented as a processing unit, such as a central processing unit (CPU), which may execute the instructions of one or more computer programs in order to implement functionality of the control unit 120.

The control unit 120 may alternatively be implemented as firmware arranged e.g. in an embedded system, or as a specifically designed processing unit, such as an Application-Specific Integrated Circuit (ASIC) or a Field-Programmable Gate Array (FPGA), which may be configured to implement functionality of the control unit 120.

The control unit 120 may be arranged on the carrier 102. In an embodiment, the control unit 120 may be arranged in a base of the carrier 102, which is not to be implanted in brain tissue during use of the neural probe 100.

The electrode arrangement 104 may further comprise a stimuli generator 130. The stimuli generator 130 may be part of the control unit 120 and may receive control signals for generating the stimulation signals that are to be provided to the electrodes 112. The control unit 120 may provide control signals corresponding to the determined stimulation signals to the stimuli generator 130 for causing the stimuli generator 130 to output the stimulation signals to the electrodes 112. However, it should be realized that the stimuli generator 130 may also be separate from the control unit 120. The stimuli generator 130 may be integrated on the carrier 102 and, in particular, the stimuli generator 130 may be arranged below the array 110 of electrodes 112. It should also be realized that more than one stimuli generator 130 may be used and that different stimuli generators 130 may be associated with different electrodes 112 in the array 110.

The stimuli generator 130 may be configured to generate stimulation signals in the form of one or more electrical pulses, but it should be realized that other waveforms may also or alternatively be used.

The electrode arrangement 104 may further comprise conductor lines 140. Each conductor line 140 may be associated with a unique electrode 112, even though only a few conductor lines 140 are indicated in FIGS. 1a-b. The stimuli generator 130 may be configured to output stimulation signals on the conductor lines 140 for providing the stimulation signals to the electrodes 112.

The conductor lines 140 may also propagate signals recorded by the electrodes 112. Recorded signals may be acquired by recording circuitry receiving the signals from the electrodes 112.

Figure 2:
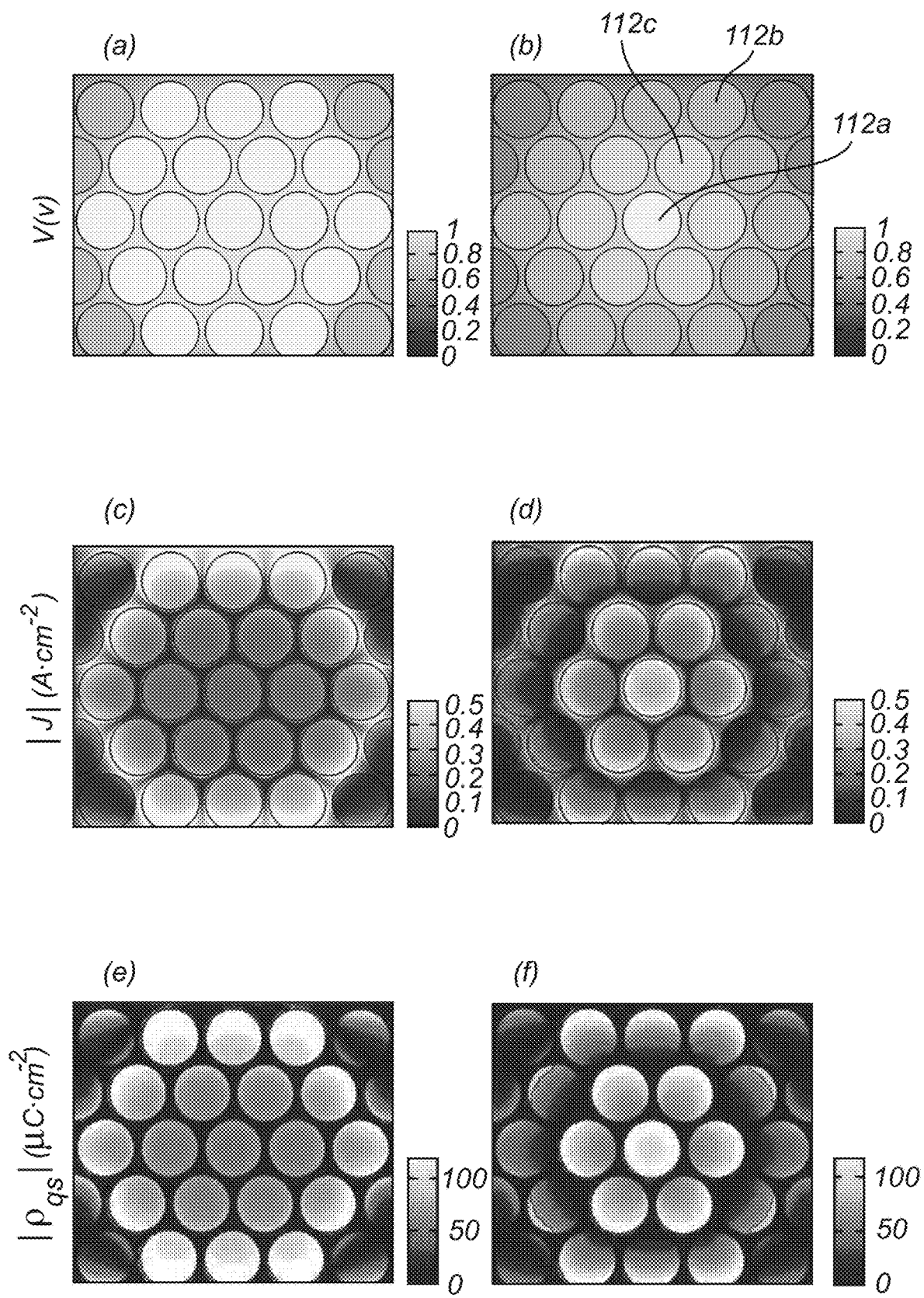
FIG. 2 shows charts of finite element method simulations illustrating current density and charge density distributions for different stimulation signals.

Referring now to FIG. 2, finite element method (FEM) simulations have been run to demonstrate an effect of providing different stimulation signals to different electrodes 112 in the combined macroelectrode site 114. In the simulations, a hexagonal combined macroelectrode site 114 is used, formed by three different sub-groups of electrodes 112: one central electrode 112a at a center of the combined macroelectrode site 114, six middle electrodes 112c surrounding the central electrode 112a, and twelve perimeter electrodes 112b at the perimeter of the combined macroelectrode site 114.

In charts (a) and (b) of FIG. 2, a magnitude of signals is indicated for the different electrodes 112a, 112b, 112c. In chart (b) optimized stimulation signals are provided, as comparison to the chart (a) for which identical stimulation signals for all electrodes are provided.

In charts (c) and (d) of FIG. 2, corresponding current density distributions over the combined macroelectrode site 114 for the stimulation signals according to charts (a) and (b) respectively are illustrated. Similarly, in charts (e) and (f) of FIG. 2, corresponding charge density distributions over the combined macroelectrode site 114 for the stimulation signals according to charts (a) and (b) respectively are illustrated.

As shown in FIG. 2, by applying different stimulation signals to the different electrodes 112a, 112b, 112c, the current density and charge density can be better distributed within the entire combined macroelectrode site 114 instead of being accumulated at an overall perimeter of the combined macroelectrode site 114. Therefore, the maximum local charge density associated with the macroelectrode site 114 is reduced.

Figure 3:
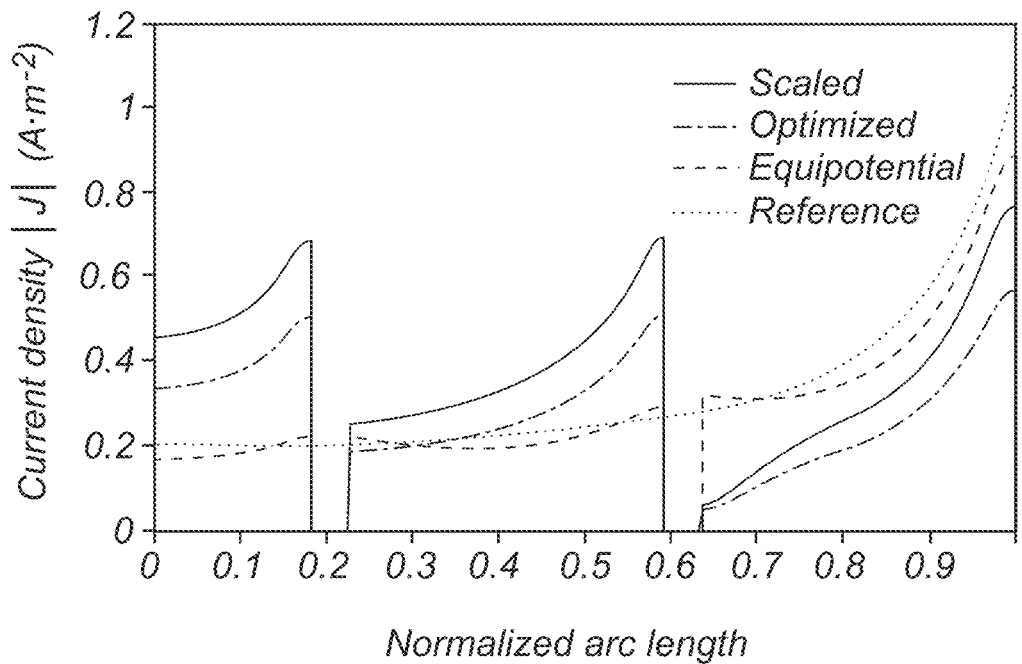
FIG. 3 is a diagram illustrating current density distribution in relation to a radial distance from a center of a macroelectrode site.

A way of comparing current uniformity along a radial direction of the combined macroelectrode site 114 is shown in FIG. 3 (wherein x-axis is a distance to a center of the combined macroelectrode site 114 and a y-axis is a current density). A reference trace (dotted line) indicates how a single large electrode of the same combined area would behave: it has low current density in the center of the electrode and a very large current density peak at the electrode perimeter. An equipotential trace (dashed line) indicates how a combined macroelectrode site provided with identical stimulation signals to all electrodes would behave: the array also has substantially larger current density peak at a perimeter of the outermost (perimeter) electrode compare to the center electrode. An optimized trace (dot-dashed line) indicates how a combined macroelectrode site 114 provided with different stimulation signals to different electrodes 112 in an optimized manner would behave, wherein the current density at the perimeter of the combined macroelectrode site 114 is substantially reduced compared to the reference trace and the equipotential trace. A scaled trace (solid line) indicates how an optimized combined macroelectrode site 114 for which the signal was scaled-up to achieve exactly the same total current as the equipotential electrode array would behave. As seen, the current density at the perimeter of the combined macroelectrode site 114 is still reduced compared to the reference trace and the equipotential trace. However, it may not be necessary to use a scaled-up signal.

Figure 4:
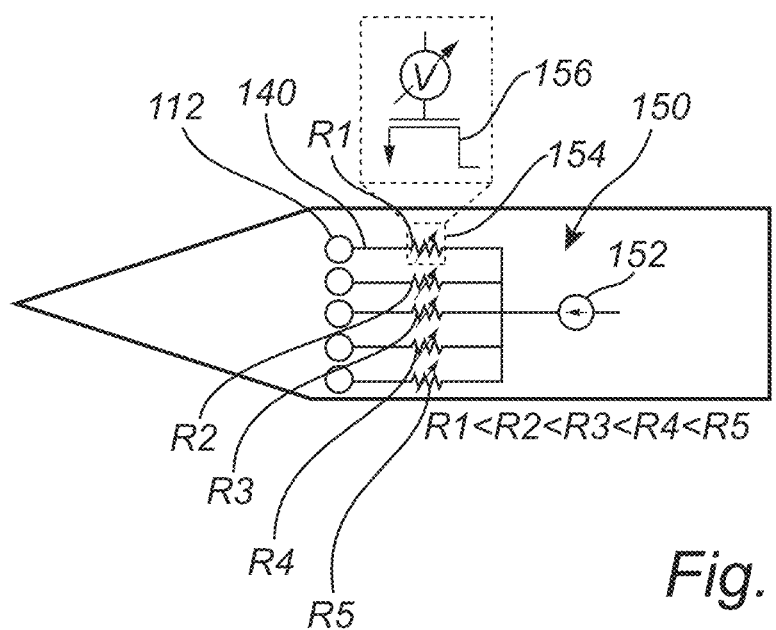
FIG. 4 is a schematic illustration of a circuitry for providing stimulation signals according to a first embodiment.

Referring now to FIG. 4, an embodiment of a circuitry 150 for providing different stimulation signals to different electrodes 112 is illustrated.

The selected plurality of electrodes 112 is configured to be connected to a common current source 152 or a common voltage source, wherein a resistance of each of the individual conductor lines 140 is tunable for controlling a magnitude of the stimulation signal received by each electrode 112 in the selected plurality of electrodes.

The circuitry 150 may comprise a tunable resistor array 154 connected to the single current source 152. The amount of current going to each electrode can be tuned by adjusting a resistance values of the tunable resistor array 154. Each resistance in the tunable resistor array 154 may be controlled using a transistor 156 with a tunable gate voltage.

Figure 5:
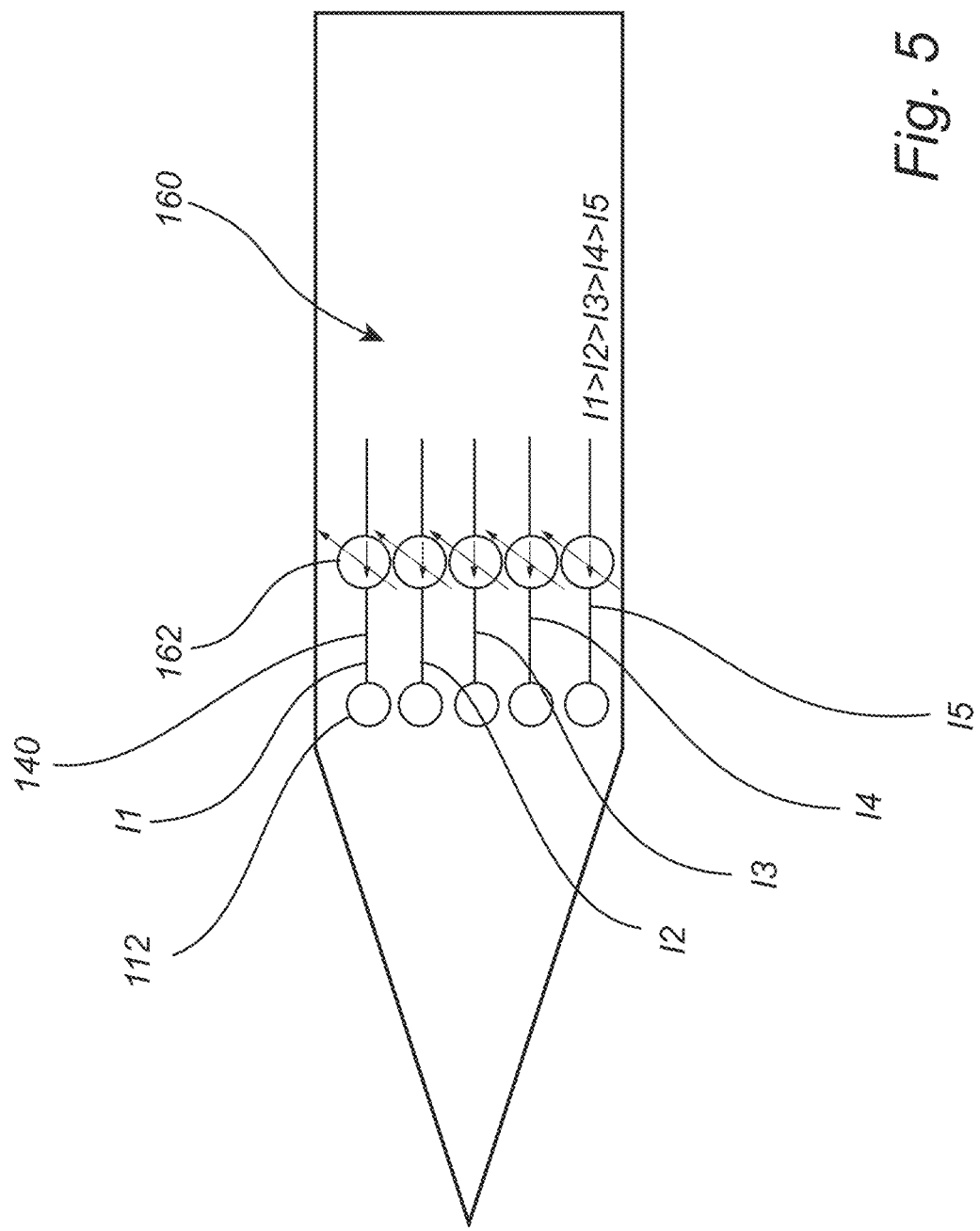
FIG. 5 is a schematic illustration of a circuitry for providing stimulation signals according to a second embodiment.

Referring now to FIG. 5, another embodiment of a circuitry 160 for providing different stimulation signals to different electrodes 112 is illustrated.

Here, each of the individual conductor lines 140 is connected to an individual programmable current source 162 or an individual programmable voltage source for controlling a magnitude of the stimulation signal received by each electrode 112 in the selected plurality of electrodes 112.

Figure 6:
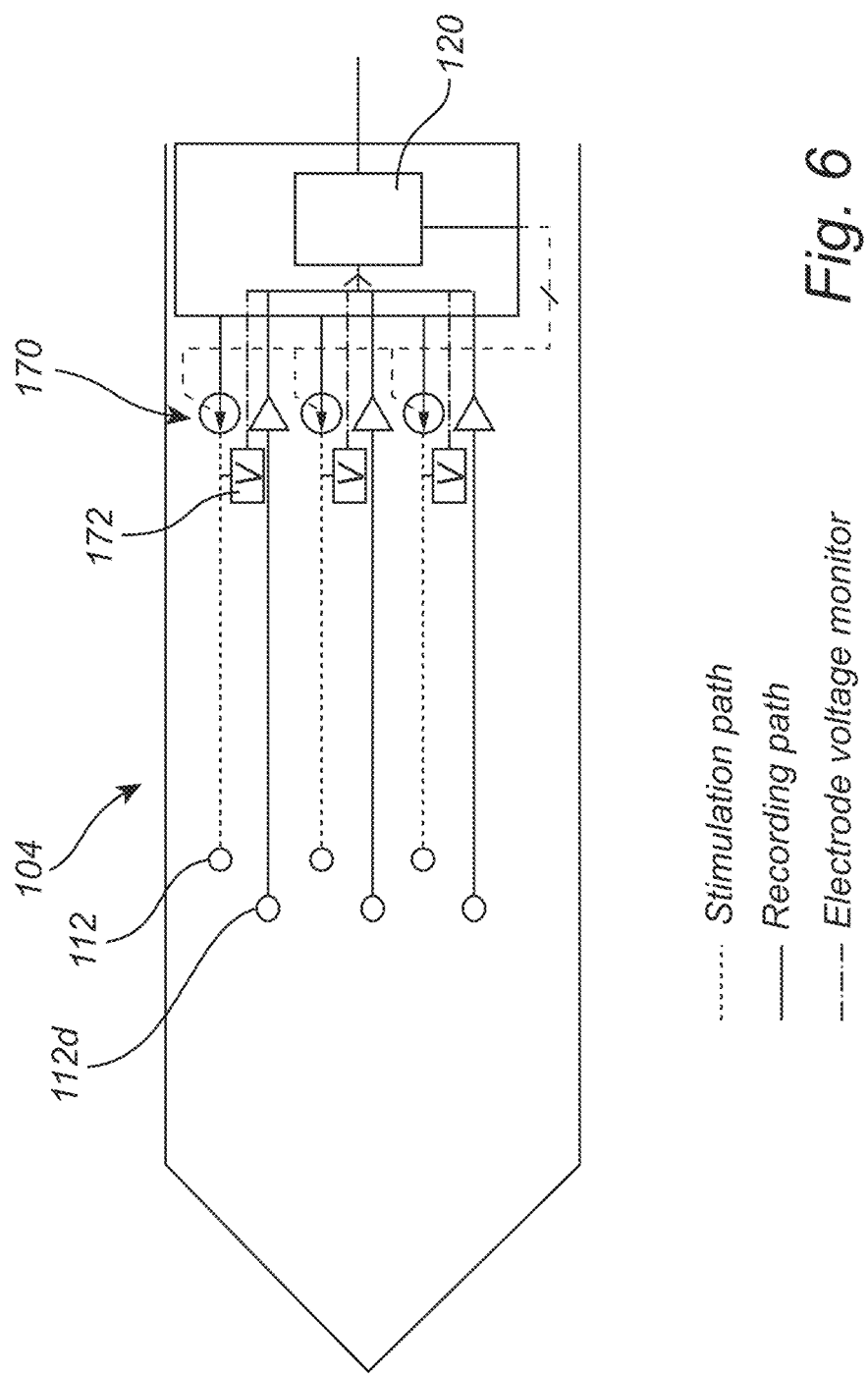
FIG. 6 is a schematic illustration of a feedback system of the electrode arrangement.

Referring now to FIG. 6, the electrode arrangement 104 may comprise a feedback system 170. The feedback system 170 may be implemented with aims of maximizing stimulation efficacy and avoiding electrode corrosion, also in presence of manufacturing spread (such as electrode dimensions, spread of electrical properties of the electrode material, routing interconnect variation between stimuli generator 130 and electrodes 112).

In a first part of the feedback system 170, the control unit 120 may vary the stimulation patterns based on the stimulation efficacy. Such stimulation efficacy can be inferred from recorded electrical signals. As discussed above, the electrodes 112 may be used both for recording signals and for providing stimulation, such that localized data recording through individual small electrodes 112 may be acquired. The localized data recording may be acquired by electrodes 112d adjacent to the electrodes 112 included in the combined macroelectrode site or by the same (or a subset of) electrodes 112 that provide stimulation signals, such that a response from the tissue is recorded.

The control unit 120 may thus receive at least one recorded feedback signal and may adapt the stimulation based on the feedback signal.

In a second part of the feedback system 170, an electrode voltage monitor 172 may be included in stimulation circuitry to permit monitoring an electrode voltage and/or impedance. For instance, the electrode voltage monitor 172 may be connected to a conductor line 140 for providing the stimulation signal to the electrode 112. Using the second part of the feedback system 170, the control unit 120 may dynamically adjust the stimulation patterns (typically a magnitude of a stimulation signal) to guarantee that electrode damage is not occurring.

The first and second part of the feedback system 170 may be used separately, such that only one of the parts of the feedback system 170 may be implemented. However, the first and second part of the feedback system 170 may also be combined, to use both stimulation efficacy and electrode monitoring concurrently as feedback variables in a dual-feedback system.

An example of using a dual-feedback system is described in the following. First, a stimulation pattern (electrode selections, stimulation amplitudes) may be determined, e.g. based on a pre-determined configuration stored in the control unit 120. Then a stimulation is applied, using the determined stimulation pattern while a stimulation efficacy is monitored using the first part of the feedback system 170. If the stimulation is determined not to be effective then, for example, stimulation amplitudes can be iteratively increased, while still ensuring that corrosion limits at the electrodes are not exceeded (based on feedback from the second part of the feedback system 170). If stimulation amplitudes are increased to the corrosion limit, and in case the stimulation efficacy is still not sufficient, then the stimulation patterns can be modified, for example by shifting a center of mass of the stimulation (electrode selection and amplitudes).

The information from the two parts of the feedback system 170 may be used to adaptively adjust weights of stimulation signals using firmware implementation of known algorithms (e.g. a least mean square (LMS) algorithm).

In addition to controlling current densities of a combined macroelectrode site 114 by varying a magnitude of a stimulation signal, steering of stimulation currents and fields may be achieved by varying waveforms, amplitudes, delays, or phase of the stimulation patterns at each electrode independently. For instance, the control unit 120 may control a phase (for an AC stimulation signal, such as a sinusoid signal) or a time delay (for pulse-based waveforms, such as monophasic, biphasic and triphasic waveforms) in addition to the magnitude (amplitude) in order to control the amount of charge injected in an electrode 112 of the combined macroelectrode site 114 at a given time interval. This opens a possibility of steering the charge or current injected to achieve a "beamforming effect" for controlling a location of injected charges in relation to the location of the combined macroelectrode site 114, in addition to a spatial steering already available by selection of different electrodes 112 that are to form the combined macroelectrode site 114.

Figure 7:
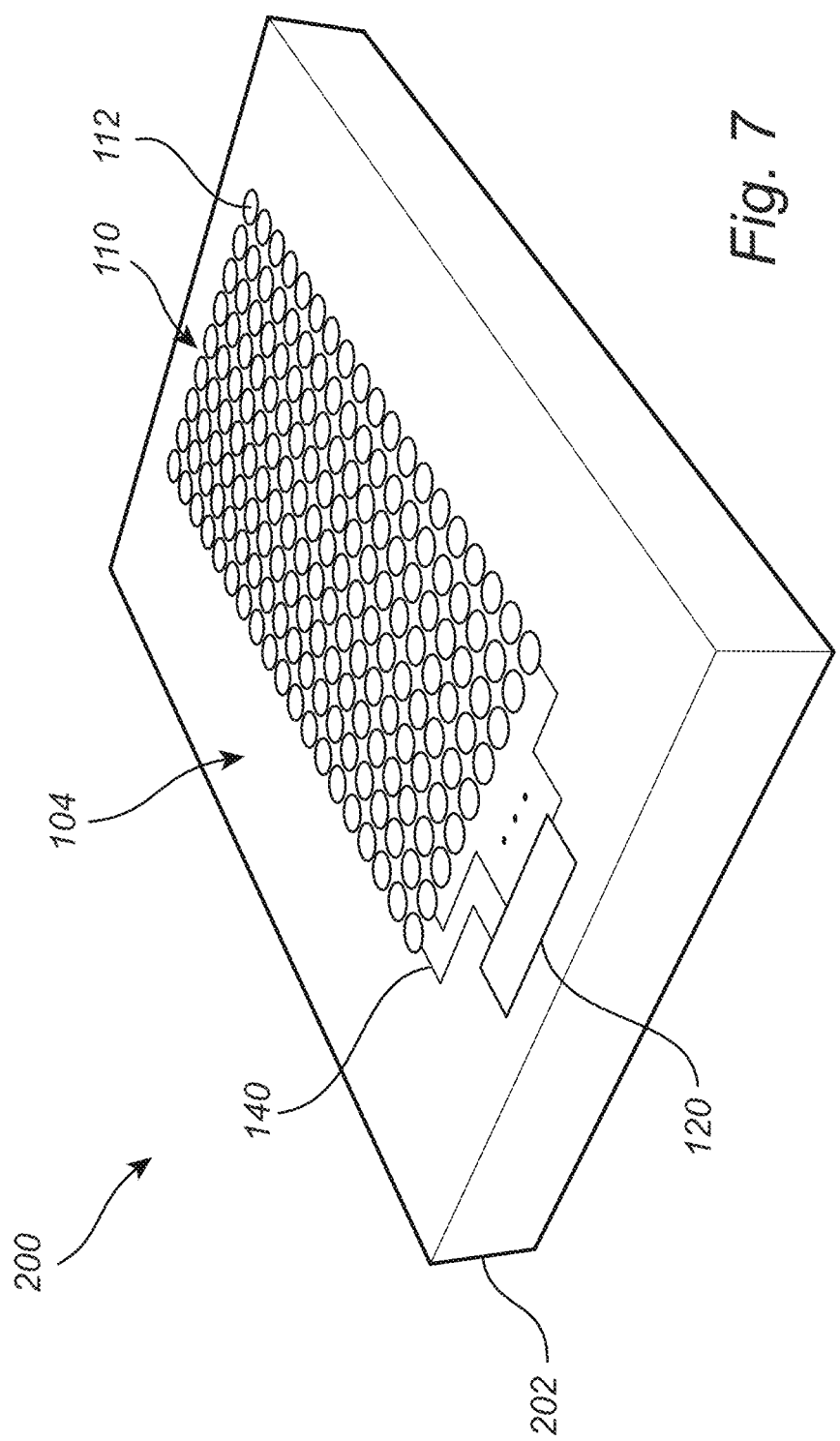
FIG. 7 is a schematic illustration of a micro-electrode array according to an embodiment.

Referring now to FIG. 7, the electrode arrangement 104 may be arranged in a micro-electrode array 200. Thus, instead of using the electrode arrangement 104 in a neural probe 100, the electrode arrangement 104 may be used in a micro-electrode array 200.

The electrode arrangement 104 may function in the same way as described above in relation to the neural probe 100.

The micro-electrode array 200 may comprise a large number of electrodes 112 for enabling stimulation and recording of electrical signals in samples of biological matter grown or provided on the micro-electrode array 200.

The micro-electrode array 200 may be used in many different ways depending e.g. on the type of cells to be analyzed. Thus, the possibility of the electrode arrangement 104 to dynamically select electrodes 112 to be included in a combined macroelectrode site 114 may enable the micro-electrode array 200 to be used in a versatile manner. Furthermore, thanks to the control unit 120 of the electrode arrangement 104 controlling stimulation signals to perimeter electrode(s) 112b and central electrode(s) 112a in macroelectrode sites 114, electrode corrosion in the micro-electrode array 200 may be avoided.

The micro-electrode array 200 may comprise a carrier 202 providing a surface for receiving a sample of biological matter and includes the array 110 of electrodes 112 of the electrode arrangement 104. The electrodes 112 of the micro-electrode array 200 may be controlled using the control unit 120 described above. The control unit 120 may be arranged adjacent to or below the array 110 of electrodes 112 provided on the carrier 202.

Figure 8:
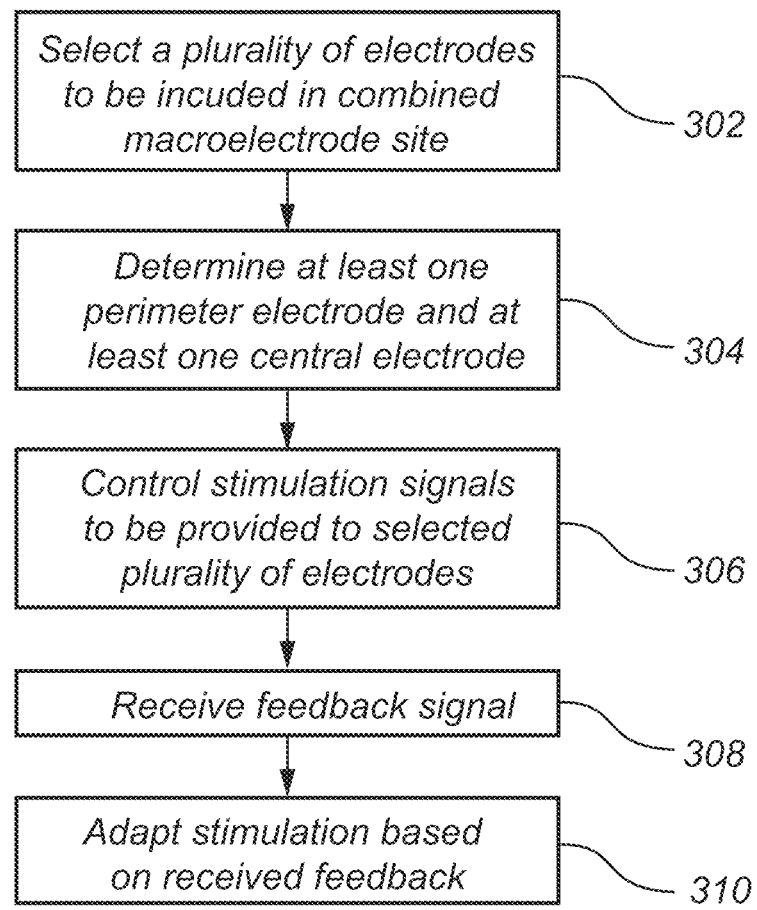
FIG. 8 is a flowchart of a method according to an embodiment.

Referring now to FIG. 8, a method of controlling the electrode arrangement 104 for stimulating and recording electrical signals in biological matter will be described.

The method comprises selecting 302 a plurality of electrodes 112 of the array 110 to be included in a group forming a combined macroelectrode site 114 for providing a stimulation signal.

The method further comprises determining 304 at least one perimeter electrode 112b within the selected plurality of electrodes 112 and at least one central electrode 112a within the selected plurality of electrodes.

The method further comprises controlling 306 stimulation signals to be provided to the selected plurality of electrodes 112, wherein the stimulation signal provided to the at least one perimeter electrode 112b has a lower magnitude than the stimulation signal provided to the at least one central electrode 112a.

The method allows dynamically defining stimulation signals for different settings of combined macroelectrode sites 114 so as to limit charge accumulation at the perimeter of the combined macroelectrode site 114 and avoid causing tissue damage and/or electrode corrosion.

The method also allows dynamically defining the combined macroelectrode site 114 so as to change a location of providing stimulation signals.

The method may also comprise receiving 308 at least one feedback electrical signal recorded from the biological matter in response to a stimulating signal and/or receiving feedback from a monitoring circuitry 172, which is associated with each electrode 112 for monitoring an electrode voltage and/or impedance of the electrode, in relation to the selected plurality of electrodes 112.

The method may further comprise adapting 310 stimulation based on the received feedback. The adapting of the stimulation may include changing a selection of electrodes 112 so as to move the location of the combined macroelectrode site 114 and/or change a shape or size of the combined macroelectrode site 114. The adapting of the stimulation may also or alternatively include changing one or more stimulation signals to the selected plurality of electrodes 112 with respect to at least one of magnitude, waveform, phase and delay of the stimulation signal.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. An electrode arrangement for stimulating and recording electrical signals in biological matter, said electrode arrangement comprising:
   an array of electrodes, wherein electrodes in the array are configured to be switchable between stimulating and recording of electrical signals; and
   a control unit for controlling functionality of electrodes in the array of electrodes,
   wherein the control unit is configured to select a plurality of electrodes of the array to be included in a group forming a combined macroelectrode site 10 for providing a stimulating signal, the selected plurality of electrodes being neighboring in the group,
   wherein the control unit is further configured to determine at least one perimeter electrode within the selected plurality of electrodes of the group and at least one central electrode within the selected plurality of electrodes of the group, wherein the perimeter electrode is arranged at a perimeter of the combined macroelectrode site and the central electrode is arranged centrally within the combined macroelectrode site, and
   wherein the control unit is further configured to provide individually controlled stimulation signals to the selected plurality of electrodes of the group, wherein the stimulation signal provided to the at least one perimeter electrode has a lower magnitude than the stimulation signal provided to the at least one central electrode.

2. The electrode arrangement according to claim 1, wherein each electrode in the array has a planar surface for contacting biological matter.

3. The electrode arrangement according to claim 1, wherein each of the electrodes in the array has an equal size and shape.

4. The electrode arrangement according to claim 1, wherein each electrode of the array is connected to an individual conductor line for receiving stimulating signals or providing recorded signals.

5. The electrode arrangement according to claim 4, wherein the selected plurality of electrodes is configured to be connected to a common current source or a common voltage source, wherein a resistance of each of the individual conductor lines is tunable for controlling a magnitude of the stimulation signal received by each electrode in the selected plurality of electrodes.

6. The electrode arrangement according to claim 4, wherein each of the individual conductor lines is connected to an individual programmable current source or an individual programmable voltage source for controlling a magnitude of the stimulation signal received by each electrode in the selected plurality of electrodes.

7. The electrode arrangement according to claim 1, wherein the control unit stores pre-determined configurations for stimulation patterns for providing stimulation signals to the selected plurality of electrodes in different settings of the group forming a combined macroelectrode site.

8. The electrode arrangement according to claim 1, wherein the control unit is configured to receive at least one feedback electrical signal recorded from the biological matter in response to a stimulating signal, wherein the control unit is further configured to adapt the individually controlled stimulation signals to the selected plurality of electrodes in dependence of the received at least one feedback electrical signal and/or adapt a selection of the plurality of electrodes of the array to be included in the group forming a combined macroelectrode site.

9. The electrode arrangement according to claim 1, further comprising monitoring circuitry, wherein the monitoring circuitry is associated with each electrode for monitoring an electrode voltage and/or impedance of the electrode, wherein the control unit is further configured to receive feedback from the monitoring circuitry in relation to the selected plurality of electrodes and to adapt the individually controlled stimulation signals to the selected plurality of electrodes in dependence of the received feedback from the monitoring circuitry.

10. The electrode arrangement according to claim 1, wherein the control unit is further configured to provide different stimulation signals to different electrodes within the selected plurality of electrodes with respect to at least one of waveform, phase and delay of the stimulation signal.

11. A neural probe comprising a carrier and the electrode arrangement according to claim 1, wherein the carrier is adapted for being inserted into neural tissue of a brain and wherein at least the array of electrodes of the electrode arrangement is arranged on the carrier.

12. A micro-electrode array, comprising a carrier providing a surface for receiving a sample of biological matter; and the electrode arrangement according to claim 1, wherein at least the array of electrodes is arranged on the carrier for recording electrical signals in the sample of biological matter.

13. A method of controlling an electrode arrangement for stimulating and recording electrical signals in biological matter, wherein the electrode arrangement comprises an array of electrodes, wherein electrodes in the array are configured to be switchable between stimulating and recording of electrical signals, said method comprising:
 selecting a plurality of electrodes of the array to be included in a group forming a combined macroelectrode site for providing a stimulation signal, the selected plurality of electrodes being neighboring in the group;
 determining at least one perimeter electrode within the selected plurality of electrodes of the group and at least one central electrode within the selected plurality of electrodes of the group, wherein the perimeter electrode is arranged at a perimeter of the combined macroelectrode site and the central electrode is arranged centrally within the combined macroelectrode site; and
 controlling stimulation signals to be provided to the selected plurality of electrodes of the group, wherein the stimulation signal provided to the at least one perimeter electrode has a lower magnitude than the stimulation signal provided to the at least one central electrode.

14. The method according to claim 13, further comprising receiving at least one feedback electrical signal recorded from the biological matter in response to a stimulating signal and/or receiving feedback from a monitoring circuitry, which is associated with each electrode for monitoring an electrode voltage and/or impedance of the electrode, in relation to the selected plurality of electrodes, and adapting stimulation based on the received feedback.

15. The method according to claim 14, wherein said adapting of simulation comprises at least one of: changing a selection of electrodes to be included in the group forming the combined macroelectrode site; and changing one or more stimulation signals to the selected plurality of electrodes with respect to at least one of magnitude, waveform, phase and delay of the stimulation signal.

* * * * *